United States Patent  
Soffer et al.

(10) Patent No.: US 9,015,630 B2
(45) Date of Patent: Apr. 21, 2015

(54) CLINICAL PHOTOGRAPHIC RECORDKEEPING SYSTEM AND ASSOCIATED METHODS

(71) Applicant: Appworx LLC, Aventura, FL (US)

(72) Inventors: Ariel D. Soffer, Aventura, FL (US); Chris Cabell, Boca Raton, FL (US)

(73) Assignee: Appworx LLC, Boca Raton, FL (US)

( * ) Notice: Subject to any disclaimer, the term of this patent is extended or adjusted under 35 U.S.C. 154(b) by 176 days.

(21) Appl. No.: 13/873,654

(22) Filed: Apr. 30, 2013

(65) Prior Publication Data

US 2013/0298082 A1 Nov. 7, 2013

Related U.S. Application Data

(60) Provisional application No. 61/640,863, filed on May 1, 2012.

(51) Int. Cl.
  *G06F 3/048* (2013.01)
  *G06F 3/0482* (2013.01)
  *G06F 19/00* (2011.01)

(52) U.S. Cl.
  CPC ............ *G06F 3/0482* (2013.01); *G06F 19/321* (2013.01); *G06F 19/3418* (2013.01)

(58) Field of Classification Search
  CPC ..................................................... G06F 19/321
  USPC .......................................................... 715/835
  See application file for complete search history.

(56) References Cited

U.S. PATENT DOCUMENTS

| 7,831,077 B2 | 11/2010 | Gering |
| 2004/0024616 A1* | 2/2004 | Spector et al. ................... 705/2 |
| 2008/0229246 A1 | 9/2008 | Squilla et al. |

* cited by examiner

*Primary Examiner* — William Titcomb
(74) *Attorney, Agent, or Firm* — Allen Dyer Doppelt Milbrath & Gilchrist, P.A.

(57) ABSTRACT

A clinical photographic recordkeeping system includes a remote storage device and at least one portable electronic device. The remote storage device stores a patient list and patient photos. The portable electronic device includes a clinical photographic recordkeeping application. Execution of the application displays the patient list from the remote storage device based on a user logging into the application, selects a patient from the patient list based on a first user input, and displays an image showing a highlighted area of the selected patient to be photographed. The image includes a flag indicating that the patient has an existing photo on the remote storage device of the highlighted area to be photographed. A camera takes a new photo of the highlighted area of the patient based on a second user input.

24 Claims, 9 Drawing Sheets

CLINICAL PHOTOGRAPHIC RECORDKEEPING SYSTEM AND ASSOCIATED METHODS

RELATED APPLICATION

This application claims the benefit of U.S. Provisional Application Ser. No. 61/640,863 filed May 1, 2012, the entire contents of which are incorporated herein by reference.

FIELD OF THE INVENTION

The present invention relates to the medical field, and more particularly, to a clinical photographic recordkeeping system and related methods.

BACKGROUND OF THE INVENTION

Clinical photographic recordkeeping is commonly used by clinicians, dermatologists, and other physicians who take photos of their patients for patient photographic documentation. This documentation includes photos of the patients before receiving treatment and photos of the patients after receiving treatment. Photos can thus tell a great deal about a patient's condition at an instant in time, and serial photos taken over a period of time illustrate a patient's response to treatment. Also, the photos may be used in diagnosis and treatment planning. In some cases, the photos may be shared with other professionals for collaboration purposes.

One approach for clinical photographic recordkeeping is based on a clinician using a standard digital camera to take patient photos. The photos from the camera are then transferred to a computer system. Typically, the digital camera includes a camera card that is used to transfer the photos. If the clinician has electronic medical records (EMR) software on the computer system receiving the photos, then the photos can be clicked and dragged into the patient's chart.

The before and after photos of a patient are typically taken on different days. Many times, the before and after photos of the area being treated on the patient needs to be aligned to better highlight the effectiveness of the treatment received by the patient. Even with digital photography, the method of positioning the camera for the after photo of the treatment area to align with the before photo of the same treatment area can be tedious and time consuming.

Another approach to clinical photographic recordkeeping requires the use of expensive specialized photography equipment, which may range from $5,000 to $15,000, for example. Canfield Scientific, Inc. is a provider of such photography equipment that includes software for managing the patient's photos. For example, once a patient's photo has been taken, the photo may then be directly stored in the patient's chart. In addition, ghosting software may be available for aligning a new photo to be taken of the treatment area with an old photo of the same treatment area.

A drawback of the above approaches for clinical photographic recordkeeping is that the photos are typically stored where the equipment is located. If a clinician has multiple offices, and is meeting a patient at a different office from where the before photos were taken, then the clinician may not be able to access the before photos unless the patient's chart was transferred to the different office. This also presents a problem for collaboration on patient photos from other clinicians if the photos are not easily accessible.

SUMMARY OF THE INVENTION

In view of the foregoing background, it is therefore an object of the present invention to make photos associated with clinical photographic recordkeeping more easily accessible.

This and other objects, features, and advantages in accordance with the present invention are provided by a clinical photographic recordkeeping system comprising a remote storage device and at least one portable electronic device. The remote storage device may be configured to store a patient list and a plurality of patient photos.

The portable electronic device may comprise a housing, a transceiver carried by the housing to communicate with the remote storage device, a display carried by the housing, a camera carried by the housing, and a processor carried by the housing and coupled to the transceiver, the display and the camera.

The processor may execute a clinical photographic recordkeeping application to perform the following: display the patient list from the remote storage device based on a user logging into the clinical photographic recordkeeping application, select a patient from the patient list based on a first user input, and display at least one image showing a highlighted area of the selected patient to be photographed. The at least one image may include a flag indicating that the patient has at least one existing photo on the remote storage device of the highlighted area to be photographed.

The camera may take a new photo of the highlighted area of the patient based on a second user input while the processor displays the at least one existing photo of the highlighted area for the user to use as a guide when taking the new photo of the highlighted area.

The remote storage device may be configured as a cloud-based storage device, for example, while being HIPPA (Health Insurance Portability and Accountability Act) complainant. The portable electronic device may be configured as an iPhone, iPod, iPad or Andriod device, for example, to provide a full-featured mobile clinical photography platform for healthcare. With the clinical photographic recordkeeping system there is no need to purchase expensive and bulky photography equipment. Since the patient photos are stored on the cloud, the clinical photographic recordkeeping system advantageously allows the user to easily access the patient photos from any location using their portable electronic device.

The portable electronic device may be for clinic use based on the user having full access to the patient list after logging into the clinical photographic recordkeeping application.

The clinical photographic recordkeeping system may further comprise an additional portable electronic device for patient use based on the patient having limited access to the patient list after logging into the clinical photographic recordkeeping application. The additional portable electronic device may provide the at least one existing photo to the remote storage device. In addition or alternatively, the additional portable electronic device may provide a follow-up photo of the highlighted area to the remote storage device for display by the portable electronic device.

The clinical photographic recordkeeping system may further comprise an additional portable electronic device for collaboration use based on a collaborator having limited access to the patient list after logging into the clinical photographic recordkeeping application. The additional portable electronic device may be used by the collaborator for providing comments on the at least one existing and new photos of the highlighted area.

The clinical photographic recordkeeping application may include a list of anatomy areas for display, with at least one of the anatomy areas corresponding to the highlighted area of the patient. The list of anatomy areas may further include a stock thumbnail or an actual photo thumbnail of the patient for each anatomy area.

The clinical photographic recordkeeping application may include a three-dimensional body for display, and selection of an anatomy area on the three-dimensional body may correspond to the highlighted area of the patient.

The clinical photographic recordkeeping application may include an opacity feature for reducing an opacity of the at least one existing photo when used as a guide, and an outline feature for outlining the at least one existing photo when used as a guide. The clinical photographic recordkeeping application may also include a grid feature for displaying a grid on a camera view corresponding to the new photo of the highlighted area.

Yet another aspect of the present invention is directed to a method for operating a clinical photographic recordkeeping system as described above. The method may comprise storing the patient list and the plurality of patient photos at the remote storage device, and operating the processor to execute the clinical photographic recordkeeping application to perform the following: display the patient list from the remote storage device based on a user logging into the clinical photographic recordkeeping application, select a patient from the patient list based on a first user input, and display at least one image showing a highlighted area of the selected patient to be photographed. The at least one image may include a flag indicating that the patient has at least one existing photo on the remote storage device of the highlighted area to be photographed. The method may further comprise operating the camera to take a new photo of the highlighted area of the patient based on a second user input while the processor displays the at least one existing photo of the highlighted area for the user to use as a guide when taking the new photo of the highlighted area.

DETAILED DESCRIPTION OF THE PREFERRED EMBODIMENTS

The present invention will now be described more fully hereinafter with reference to the accompanying drawings, in which preferred embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like numbers refer to like elements throughout.

Figure 1:
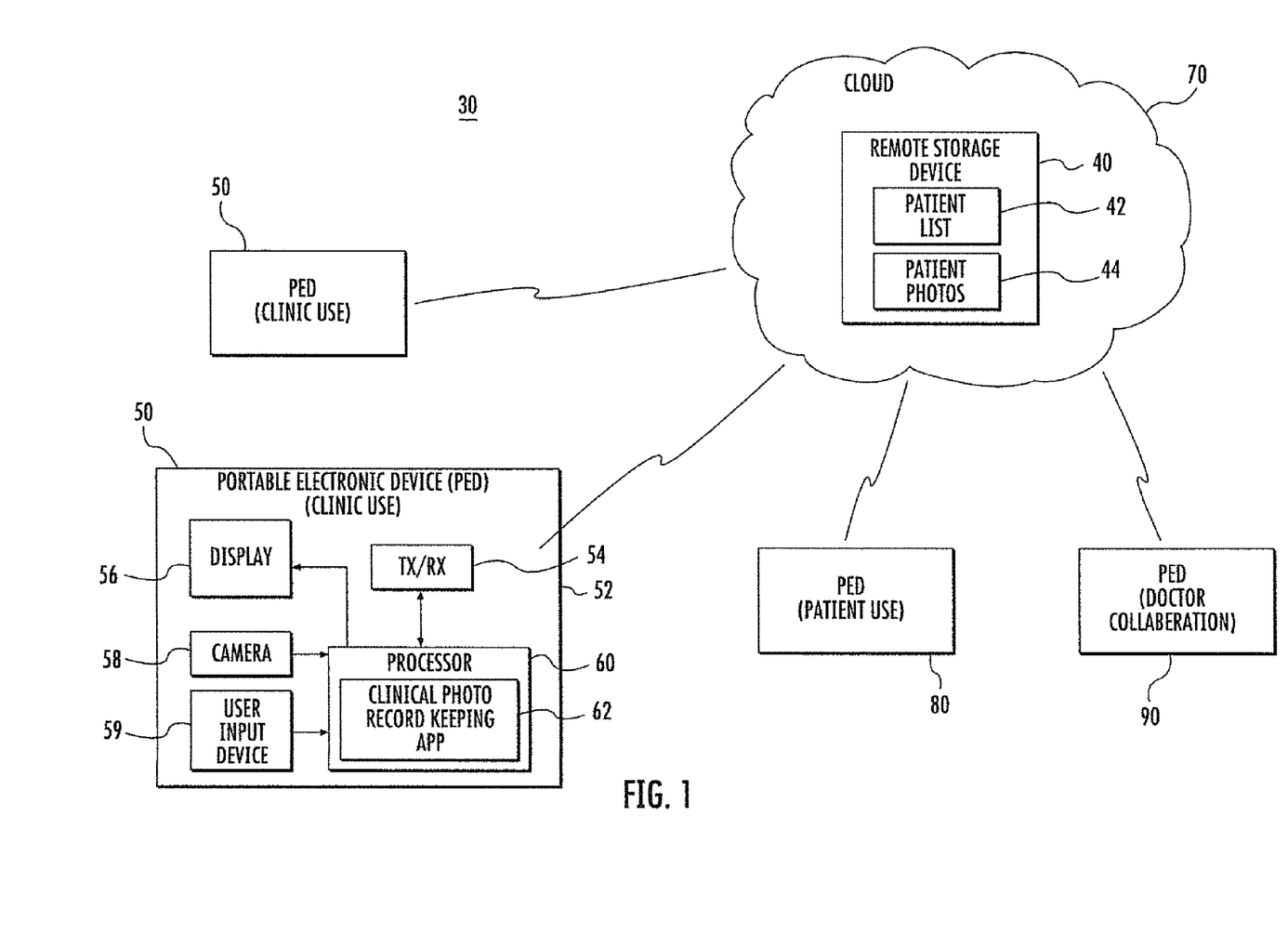
FIG. 1 is a block diagram of a clinical photographic recordkeeping system in accordance with the present invention.

Referring initially to FIG. 1, a clinical photographic recordkeeping system 30 includes a remote storage device 40 and at least one portable electronic device 50. The remote storage device 40 is configured to store a patient list 42 and patient photos 44.

The portable electronic device 50 may comprise a housing 52, a transceiver 54 carried by the housing to communicate with the remote storage device 40, a display 56 carried by the housing, a camera 58 carried by the housing, and a processor 60 carried by the housing and coupled to the transceiver, the display and the camera.

The processor 60 is configured to execute a clinical photographic recordkeeping application 62 to perform the following: display the patient list 42 from the remote storage device 40 based on a user logging into the clinical photographic recordkeeping application 62, select a patient from the patient list based on a first user input, and display at least one image showing a highlighted area of the selected patient to be photographed. The at least one image may include a flag indicating that the patient has at least one existing photo on the remote storage device 40 of the highlighted area to be photographed.

The camera 58 is configured to take a new photo of the highlighted area of the patient based on a second user input while the processor 60 is further configured to display the at least one existing photo of the highlighted area for the user to use as a guide when taking the new photo of the highlighted area.

A user input device 59, such as a keypad, is also coupled to the processor 60. The first and second user inputs may be from the same user that logged into the clinical photographic recordkeeping application 62. Alternatively, the first or second user inputs may be a different user that logged into the clinical photographic recordkeeping application 62.

The remote storage device 40 is typically at a different location than where the portable electronic device 50 is located. For example, the remote storage device 40 is configured as part of the cloud 70, for example. Nonetheless, the remote storage device 40 may be collocated with the portable electronic device 50. Communications between the remote storage device 40 and the portable electronic device 50 is encrypted to be HIPPA (Health Insurance Portability and Accountability Act) complainant. To be HIPPA compliant, the clinical photographic recordkeeping system 30 includes encryption, an encrypted firewall, and role-based security to give users different levels of access based on their roles.

The portable electronic device 50 may be configured as an iPhone, iPod, iPad or Andriod device, for example, to provide a full-featured mobile clinical photography platform for healthcare. With the clinical photographic recordkeeping system 30, there is no need to purchase expensive and bulky photography equipment. Since the patient photos 44 are stored on the cloud 70, the clinical photographic recordkeeping system advantageously allows the user to easily access the patient photos from any location using their portable electronic device 50.

In the illustrated embodiment, the portable electronic device 50 is at the clinic where the patient is being treated. Depending on the size of the clinic, there may be multiple portable electronic devices 50 in use.

The clinical photographic recordkeeping application 62 may also be downloaded to a portable electronic device 80 carried by the patient. The patient gateway implementation of the clinical photographic recordkeeping application 62 does not allow the patient to have access to the patient list 42 other than information directed to themselves. As readily appreciate by those skilled in the art, role-based security of the clinical photographic recordkeeping application 62 gives users different levels of access based on their roles.

The patient gateway implementation of the clinical photographic recordkeeping application 62 allows the patient to send photos and communicate directly with the clinic. For example, after the patient receives treatment and leaves the clinic, the patient is able to send follow-up photos of the area being treated to the remote storage device 40. This then allows the doctor or his staff at the clinic to evaluate the effectiveness of the treatment without having the patent come into the clinic. Also, if the patient is a new patient and wants to see the doctor for an initial consultation, the patient may access the clinical photographic recordkeeping application 62 to upload to the remote storage device 40 a photo that they took before actually seeing the doctor. The photo is of the area that needs to be treated.

For collaboration purposes, the clinical photographic recordkeeping application 62 may also be downloaded to a portable electronic device 90 carried by doctors not directly involved at the same clinic. For example, if the doctor treating the patient needs a second opinion, then a request may be made to another doctor using the photographic recordkeeping application 62. This request is secure and avoids the use of regular emails and texting. As part of the collaboration, the other doctor is able to retrieve the patient's photos from the remote storage device 40 and provide comments as needed. This is done without the doctor having full access to the patient list 42.

For example, the patient has a mole on their skin, and visits their primary care physician. The primary care physician uses the clinical photographic recordkeeping application 62 to store an initial photo of the mole. The primary care physician may refer the patient to a dermatologist. The dermatologist then uses the clinical photographic recordkeeping application 62 to retrieve and review the initial photo of the mole.

Figure 2:
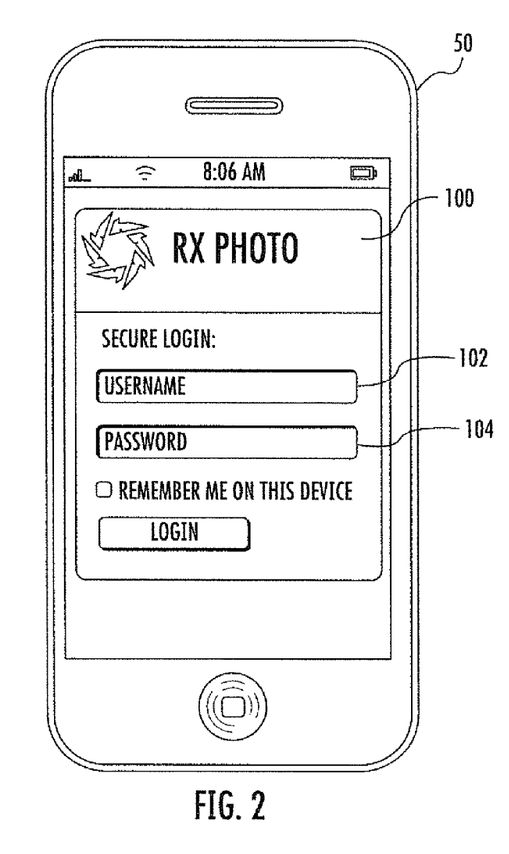
FIG. 2 is a login screen displayed on the portable electronic device illustrated in FIG. 1.

Referring now to FIGS. 2-11, operation and the various features of the photographic recordkeeping application 62 will be discussed. In the illustrated embodiment, the portable electronic device 50 is configured as an iPhone. To access the photographic recordkeeping application 62, a login screen 100 is displayed, as shown in FIG. 2. The login screen 100 includes a username field 102 and a password field 104.

Figure 3:
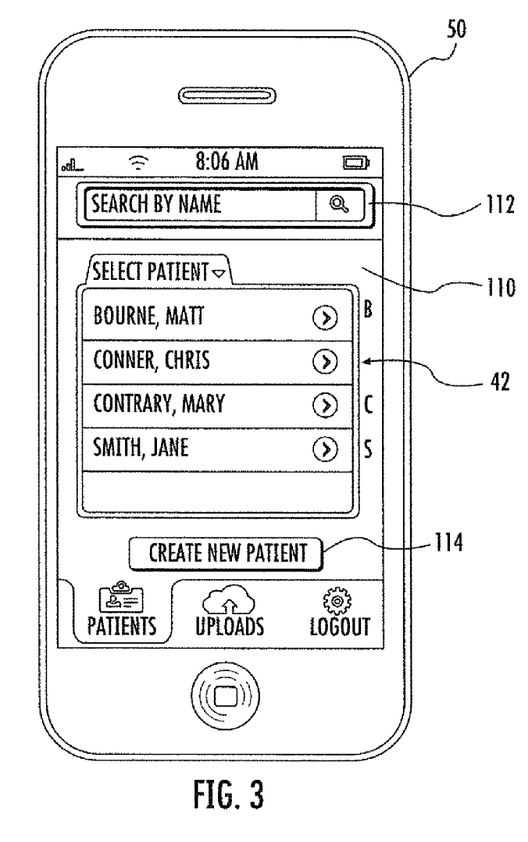
FIG. 3 is a patient list screen displayed on the portable electronic device illustrated in FIG. 1.

For discussion purposes, the user is assumed to be the doctor. Nonetheless, the user may be a member of the doctor's staff. Once the doctor is logged in, subsequent information to be displayed as related to a patient list 42 and patient photos 44 is retrieved from the remote storage device 40. A patient list screen 110 as shown in FIG. 3 provides the patient list 42.

To search for a particular patient, the doctor can scroll through the displayed patient list 42, or enter the patient's name in the search by name field 112. For a new patient, the doctor selects the create new patient field 114.

Figure 4:
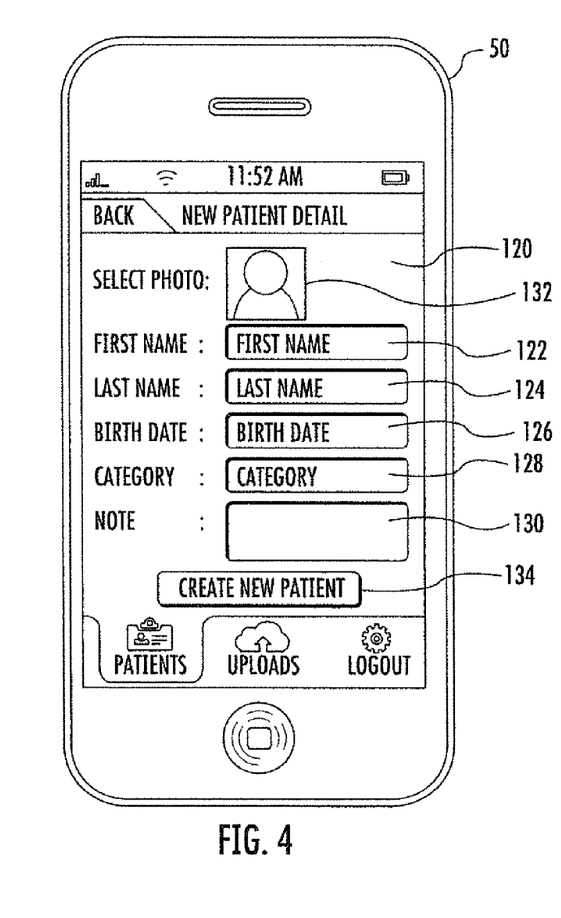
FIG. 4 is a new patient screen displayed on the portable electronic device illustrated in FIG. 1.

If the doctor selects the create new patient field 114, then new patient screen 120 is displayed, as shown in FIG. 4. The doctor enters the patient's name and birth date in fields 122, 124 and 126. A category may be selected in category field 128, and notes may be added in notes field 130. When the category field 128 is selected, the doctor has a list of displayed options to select from in order to more closely descript the type of treatment the patent is to receive. For example, if the patent is to receive treatment for their veins, then the doctor can select from the following vein disease categories: C0—no vein pathology, C1—spider or reticular veins, C2—varicose veins, C3—edema with veins, C4—skin change, no ulceration.

The doctor also has the option of adding a picture of the patent. This is accomplished by the doctor selecting the select photo field 132 and using the portable electronic device 50 to take the patient's picture. Once the information has been entered, then the create new patient field 134 is selected by the doctor.

Figure 5:
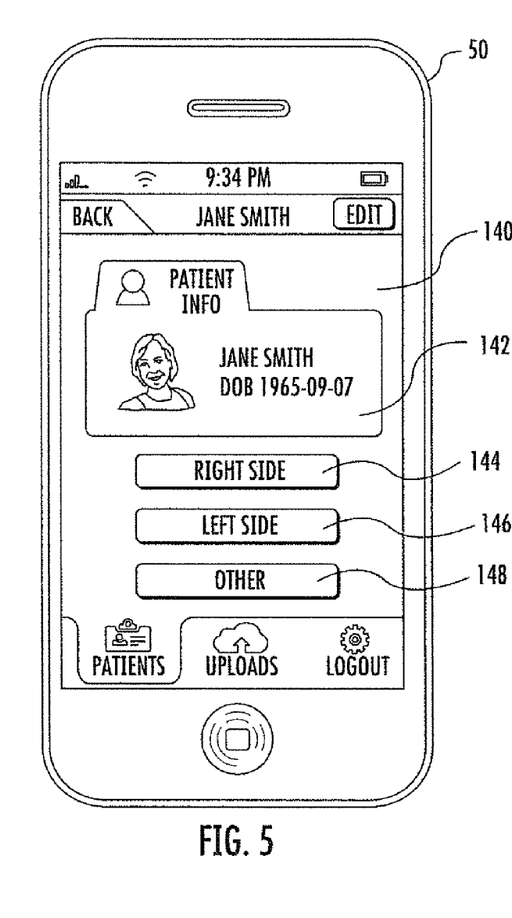
FIG. 5 is a patient profile screen displayed on the portable electronic device illustrated in FIG. 1.

When the doctor selects a patient on the patient list 42, as displayed in FIG. 3, then a patient profile screen 140 for the selected patient is displayed, as shown in FIG. 5. In addition to the patient info field 142, the doctor also has the option of selecting from broad anatomy areas to narrow down the area of treatment for the patient. The right side field 144 corresponds to the right side of the body, the left side field 146 corresponds to the left side of the body, and the other field 146 corresponds to a more central area of the body, such as the head or mid-section, for example.

Figure 6:
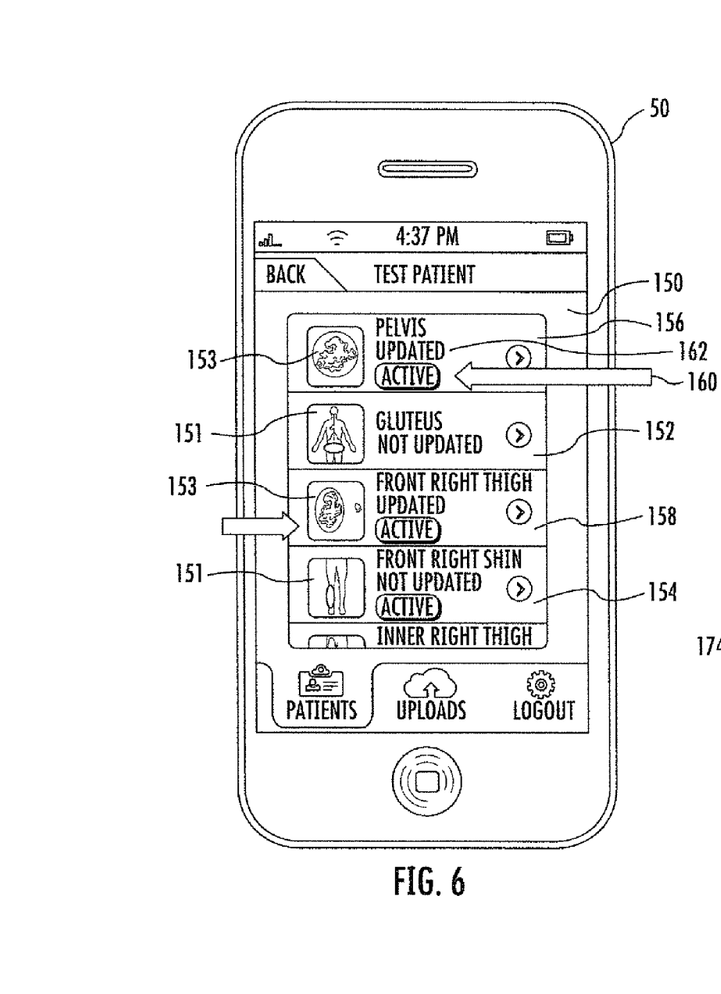
FIG. 6 is a list of patient images screen displayed on the portable electronic device illustrated in FIG. 1.

Depending on which of the fields the doctor selects, a list of patient images screen 150 is displayed, as shown in FIG. 6. The illustrated list of patient images screen 150 includes a number of different thumbnails corresponding to the different parts of the body. Each part of the body may correspond to a cataloged anatomy area. The thumbnails may be stock thumbnails 151 or actual photo thumbnails 153. For example, stock thumbnails 151 are used for the gluteus image field 152 and the front right shin image field 154. For example, actual photo thumbnails 153 are used for the pelvis image field 156 and the right front thigh image field 158.

From the patient images screen 150, the doctor can scroll up or down to view all of the cataloged anatomy areas. The cataloged anatomy areas allow the doctor to easily label the photos. For the photographic recordkeeping application 62, there are about 180 cataloged anatomy areas the doctor can select from. The actual number of cataloged anatomy areas will vary depending on the level of detail of the body as provided by the clinical photographic recordkeeping application 62.

The list of patient images screen 150 also tells the doctor if previous photos are available for the selected patient, as well as what image fields have been updated during the patient's current visit. An active flag 160 tells the doctor that previous photos are available for this patient. When the doctor uploads a new image to the remote storage device 40, the status of this field changes to updated, as indicated by reference 162.

Figure 7:
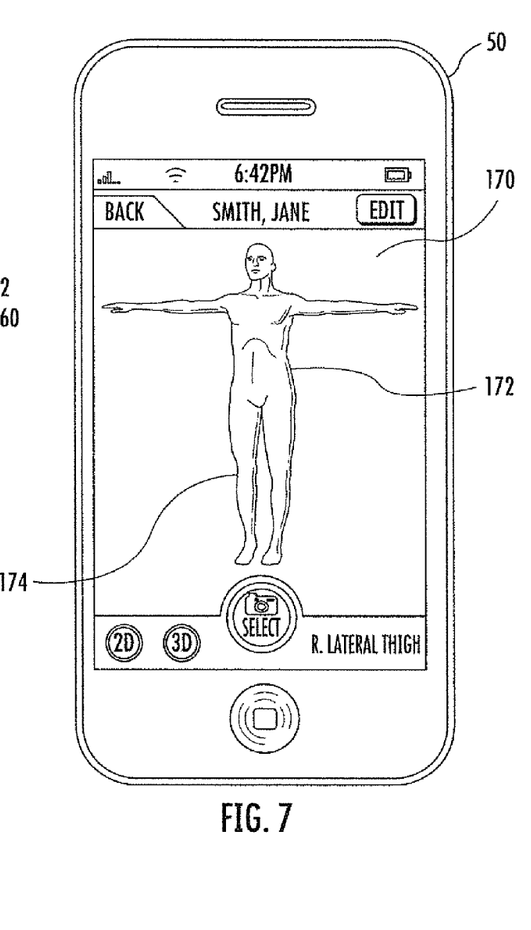
FIG. 7 is a three-dimensional (3D) profile image screen displayed on the portable electronic device illustrated in FIG. 1.

As an alternative to scrolling through the list of cataloged anatomy areas, the doctor has the option of viewing a three-dimensional (3D) profile image screen 170 representing the patient's body 172, as illustrated in FIG. 7. The illustrated body 172 is a generic template to assist the doctor for selection of the anatomy areas to be photographed.

Figure 8:
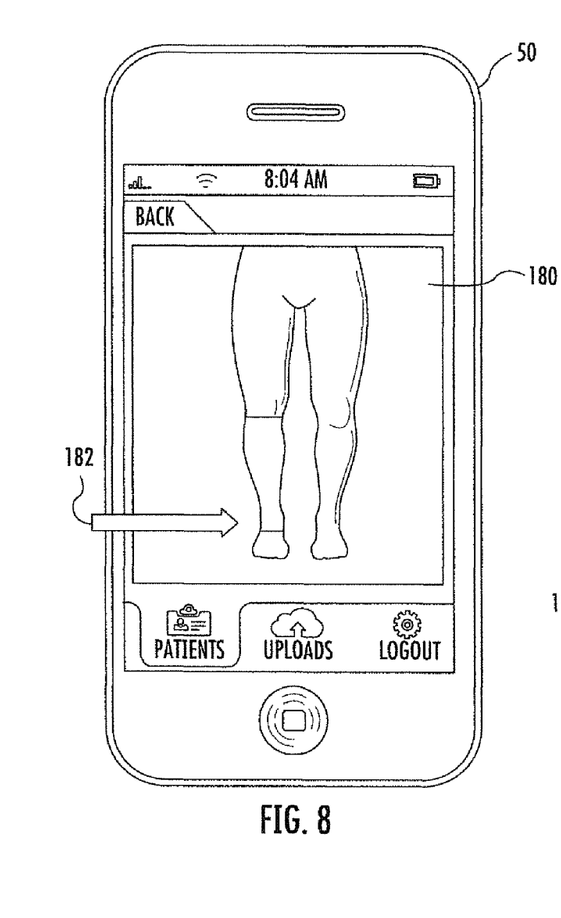
FIG. 8 is a photo guide image screen displayed on the portable electronic device illustrated in FIG. 1.

To take a photo of the desired area to be treated, the doctor selects or taps on the corresponding location on the body 172. If the patent is seeing the doctor to receive treatment for their veins in their right leg, then the doctor selects the right side 174 of the body 172. If the right side 174 is selected, then a photo guide image screen 180 is provided to show the doctor which treatment area is to be photographed, as illustrated in FIG. 8. The treatment area 182 is highlighted in a different color, such as red, for example.

Figure 9:
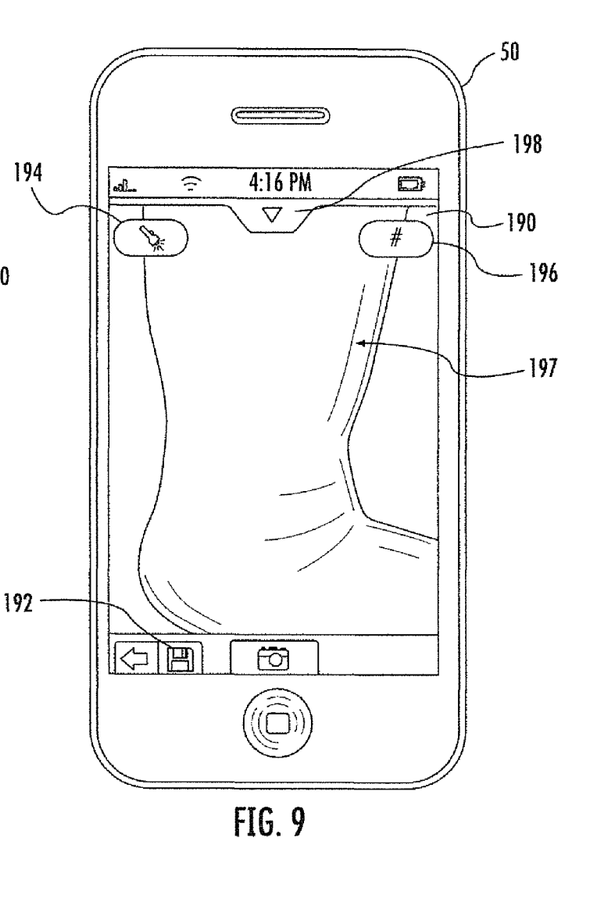
FIG. 9 is a camera view screen shot as displayed on the portable electronic device illustrated in FIG. 1.

The highlighted treatment area 182 is a general tool and the composition of the photo can vary based on the actual treatment area. To take a picture or view a previous photo, the doctor touches the highlighted treatment area 182. This lead to a displayed camera view 190, as illustrated in FIG. 9. The patient's right leg is now being displayed since the camera 58 is pointed in that direction. In this camera view 190, the doctor has a number of options. Library icon field 192 allows the doctor to add photos from a library within the personal electronic device 50. The flashlight icon field 194 allows the doctor to turn on or off the camera's flash. The photo grid icon field 196 allows the doctor to turn on and off a displayed grid 197 to aid in the proper composition of the photo. In the illustrated example, the grid 197 is turned on. The previous photo tab field 198 tells the doctor that there is at least one previous photo of this body part available from the remote storage unit 40. The previous photo tab field 198 will not be visible if there are no previous photos.

Figure 10:
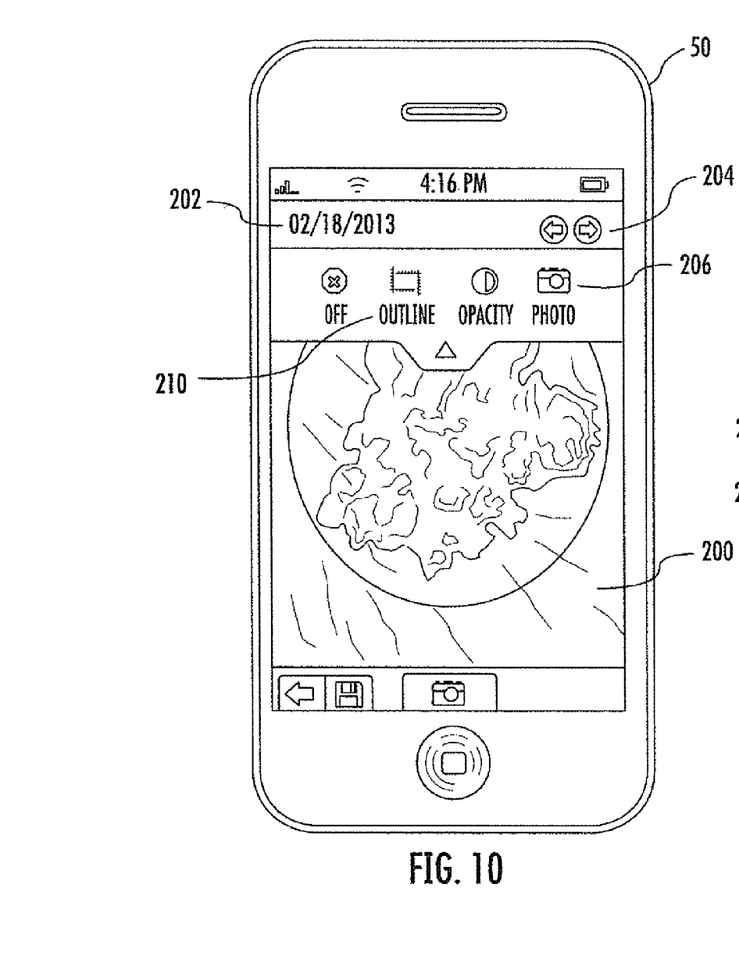
FIG. 10 is a previous photo displayed on the portable electronic device illustrated in FIG. 1.

If the doctor selects the previous photo tab field 198, then the latest previous photo is displayed in the previous photo screen 200, as illustrated in FIG. 10. This screen includes a date field 202 on when the previous photo was taken. If more than one previous photo is available, arrows 204 allow the doctor to view the different photos. The arrows 204 will not appear if only one previous photo is available. The photo icon field 206 also allows the doctor to view a previous photo.

Figure 11:
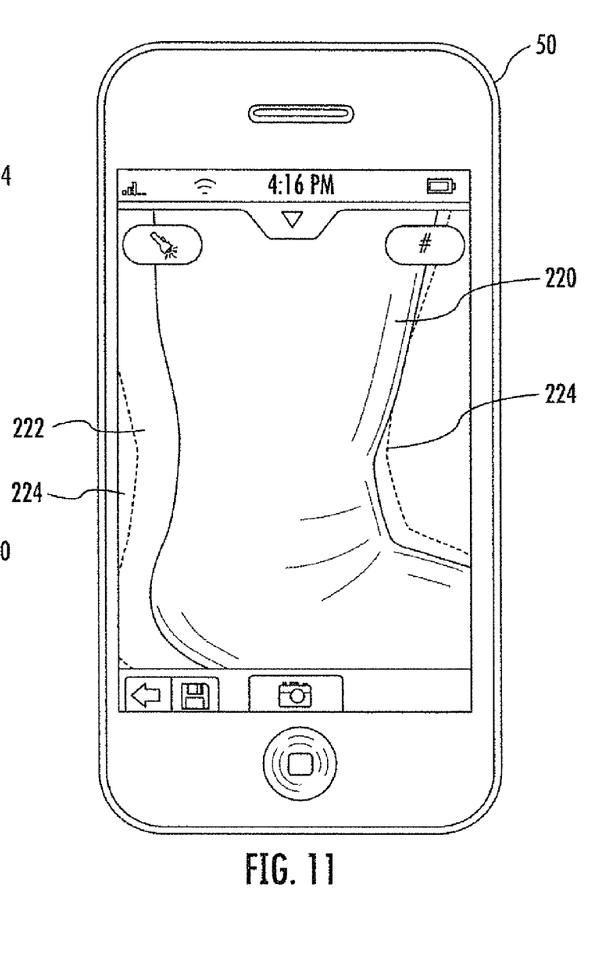
FIG. 11 is an opacity and outline overlay of a previous photo displayed on a camera view corresponding to the new photo to be taken by the portable electronic device illustrated in FIG. 1.

The opacity icon field 208 shows a previous photo at a certain opacity, such as 70%, for example. The opacity may be predefined at 70%, or the percentage may be changed or selected by the doctor. Changing the opacity of the previous photo causes it to become more transparent or translucence. As the opacity percentage is lowered, the previous photo becomes more see-through. This advantageously allows the doctor to overlay the previous photo on the camera view so that the doctor can take a consistent new photo, as illustrated in FIG. 11. A current view of the patient's right ankle is indicated by reference 220, and the previous photo at 70% opacity is indicated by reference 222. The outline icon field 210 creates an outline of the previous photo by highlighting the dark edges, as indicated by reference 224.

Figure 12:
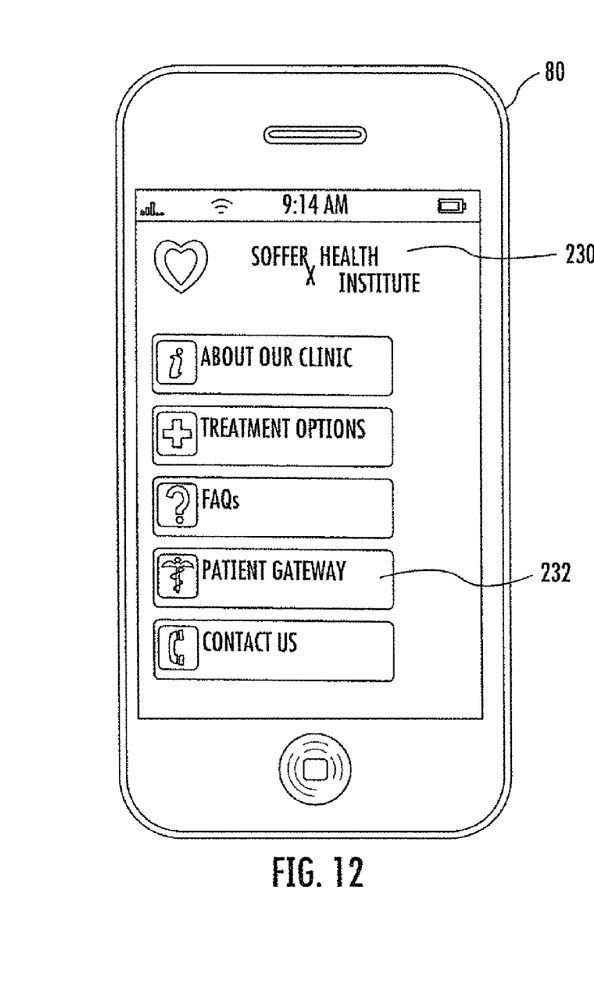
FIG. 12 is an initial patient screen displayed on the patient portable electronic device illustrated in FIG. 1.

As discussed above, the clinical photographic recordkeeping application 62 may also be downloaded to a portable electronic device 80 carried by the patient. Once downloaded, an initial patient screen 230, as illustrated in FIG. 12, allows the patient to select the patient gateway field 232.

Figure 13:
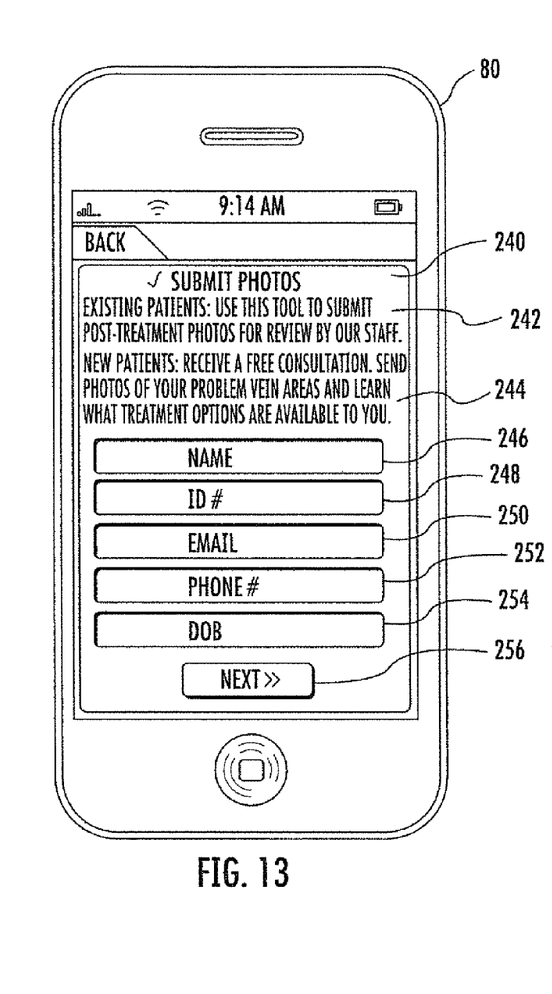
FIG. 13 is a submit photo screen displayed on the patient portable electronic device illustrated in FIG. 1.

The patient has the option of submitting photos, as indicated by the submit photo screen 240 illustrated in FIG. 13. The submit photo screen 240 indicates that the patient may be an existing patient as indicated in existing patient field 242, where the patient can submit post-treatment photos for review by the doctor and his staff. The submit photo screen 240 also indicates that a new patient may receive a free consultation, as indicated by new patient field 244, by sending photos of the problem area so as to learn what treatment options are available. The patient is required to fill in the required fields, including the following: name field 246, ID number field 248, email field 250, phone number field 252 and date of birth field 254. Alternatively, the ID number field 248 may be automatically filled in by the clinical photographic recordkeeping application 62.

Figure 14:
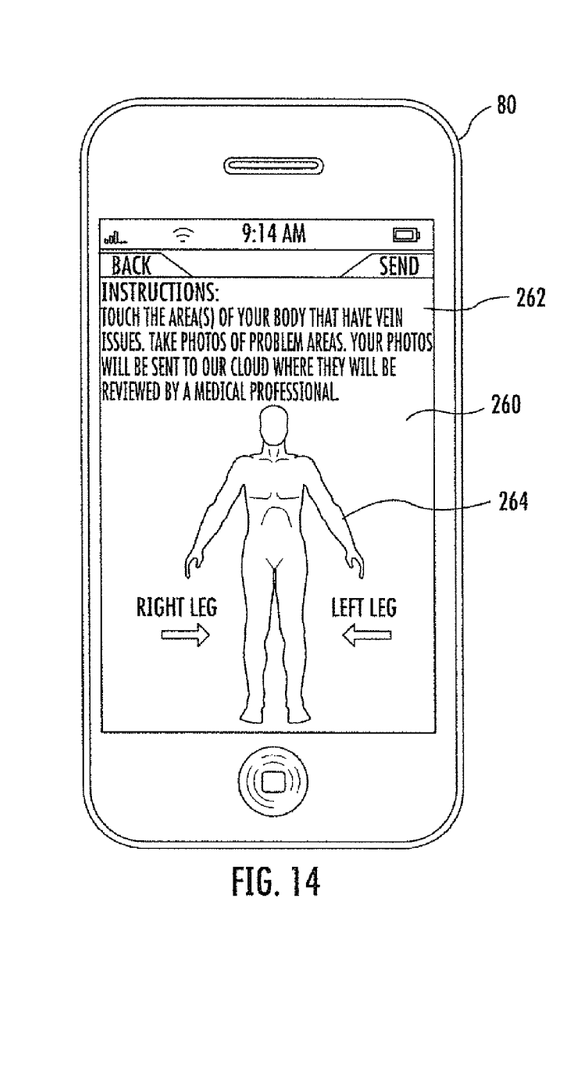
FIG. 14 is a photo instructions screen displayed on the patient portable electronic device illustrated in FIG. 1.
Figure 15:
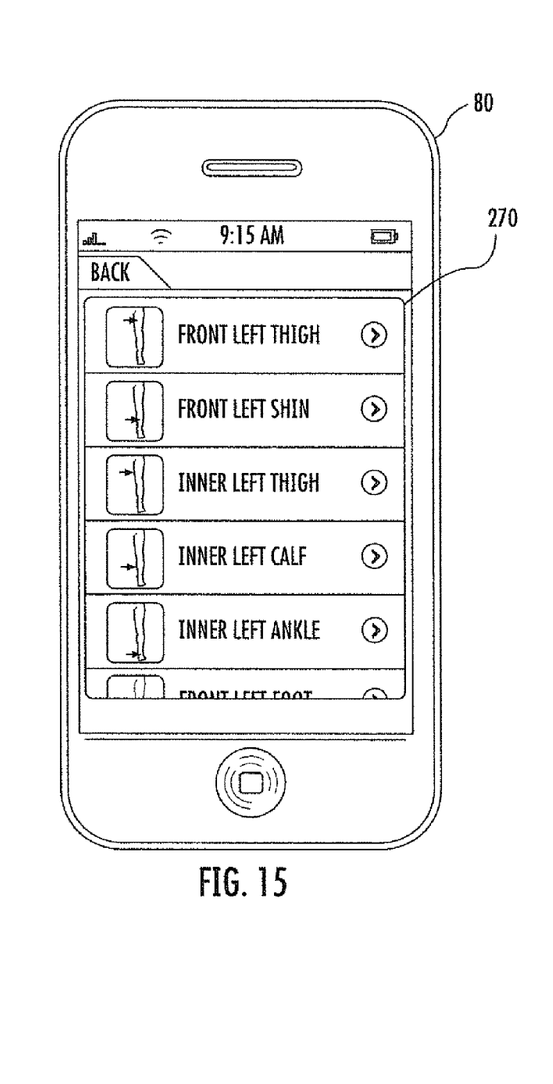
FIG. 15 is an anatomy list screen displayed on the patient portable electronic device illustrated in FIG. 1.

After the required information has been entered, the next field 256 is selected by the patient. This provides the photo instructions screen 260, as illustrated in FIG. 14. The instructions field 262 instructs the patient to touch the area(s) of the illustrated body 264 that have issues, and to take photos of the problem areas. If the patient selects the left leg or right leg of the illustrated body 264, then a corresponding anatomy list screen 270 appears, as illustrated in FIG. 15. The patient selects the particular anatomy area of concern prior to taking the photos. As the photos are taken, they are sent to the remote storage device 40 for review.

The patient application advantageously allows the patient to have a direct link to the doctor's patient portal or website. The patient can ask questions about areas of concern (i.e., new veins or post surgery and healing process) by simply taking photos of the troubled area and uploading to the remote storage device 40. This process is then seamlessly integrated in the cloud 70 and simultaneously notifies the doctor for immediate review and response.

Figure 16:
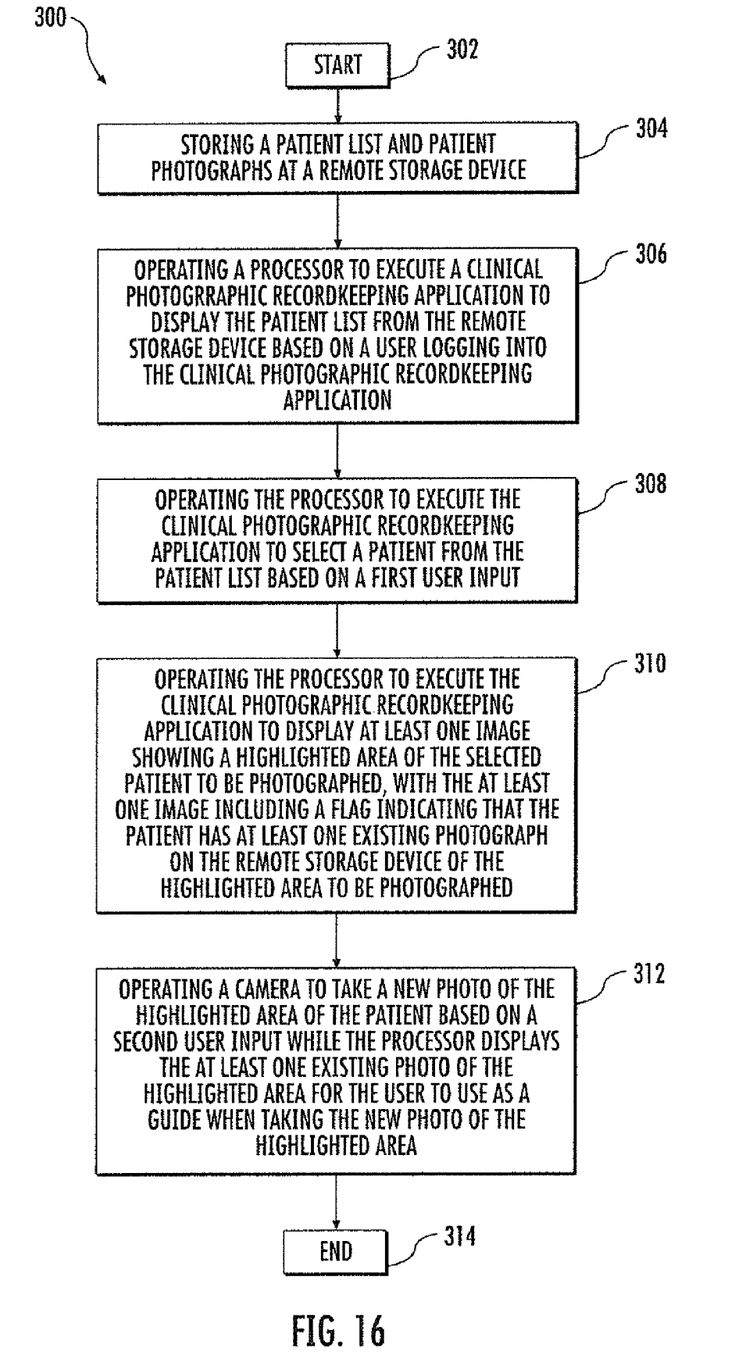
FIG. 16 is a flowchart illustrating a method for operating a clinical photographic recordkeeping system as illustrated in FIG. 1.

Referring now to the flowchart 300 in FIG. 16, another aspect is directed to a method for operating the clinical photographic recordkeeping system 30. The method comprises, from the start (Block 302), storing a patient list 42 and a plurality of patient photo 44 at the remote storage device 70 at Block 304. The processor 60 is operated at Block 306 to execute the clinical photographic recordkeeping application 62 to display the patient list 42 from the remote storage device 40 based on a user logging into the clinical photographic recordkeeping application 62. The processor 60 is operated at Block 308 to execute the clinical photographic recordkeeping application 62 to select a patient from the patient list 42 based on a first user input. The processor 60 is operated at Block 310 to execute the clinical photographic recordkeeping application 62 to display at least one image showing a highlighted area of the selected patient to be photographed. The at least one image may include a flag 160 indicating that the patient has at least one existing photo on the remote storage device 40 of the highlighted area to be photographed. The method further includes at Block 312 operating the camera 58 to take a new photo of the highlighted area of the patient based on a second user input while the processor 60 causes the at least one existing photo of the highlighted area to be displayed for the user to use as a guide when taking the new photo of the highlighted area. The method ends at Block 314.

Many modifications and other embodiments of the invention will come to the mind of one skilled in the art having the benefit of the teachings presented in the foregoing descriptions and the associated drawings. Therefore, it is understood that the invention is not to be limited to the specific embodiments disclosed, and that modifications and embodiments are intended to be included within the scope of the appended claims.

That which is claimed is:

1. A clinical photographic recordkeeping system comprising:
   a remote storage device configured to store a patient list and a plurality of patient photos; and
   at least one portable electronic device comprising
      a housing,
      a transceiver carried by said housing and configured to communicate with said remote storage device,
      a display carried by said housing,
      a camera carried by said housing, and a processor carried by said housing and coupled to said transceiver, said display and said camera, said processor configured to execute a clinical photographic recordkeeping application to perform the following display the patient list from said remote storage device based on a user logging into said clinical photographic recordkeeping application, select a patient from the patient list based on a first user input, and display at least one image showing a highlighted area of the selected patient to be photographed, with the at least one image including a flag indicating that the patient has at least one existing photo on said remote storage device of the highlighted area to be photographed, and said camera configured to take a new photo of the highlighted area of the patient based on a second user input while said processor is further configured to display the at least one existing photo of the highlighted area for the user to use as a guide when taking the new photo of the highlighted area.

2. The clinical photographic recordkeeping system according to claim 1 wherein said remote storage device is configured as a cloud-based storage device.

3. The clinical photographic recordkeeping system according to claim 1 wherein said at least one portable electronic device is for clinic use based on the user having full access to the patient list after logging into said clinical photographic recordkeeping application.

4. The clinical photographic recordkeeping system according to claim 3 further comprising at least one additional portable electronic device for patient use based on the patient having limited access to the patient list after logging into said clinical photographic recordkeeping application, with said at least one additional portable electronic device providing the at least one existing photo to said remote storage device.

5. The clinical photographic recordkeeping system according to claim 3 further comprising at least one additional portable electronic device for patient use based on the patient having limited access to the patient list after logging into said clinical photographic recordkeeping application, with said at least one additional portable electronic device providing a follow-up photo of the highlighted area to said remote storage device for display by said at least one portable electronic device.

6. The clinical photographic recordkeeping system according to claim 3 further comprising at least one additional portable electronic device for collaboration use based on a collaborator having limited access to the patient list after logging into said clinical photographic recordkeeping application, with said at least one additional portable electronic device being used by the collaborator for providing comments on the at least one existing and new photos of the highlighted area.

7. The clinical photographic recordkeeping system according to claim 1 wherein said clinical photographic recordkeeping application includes a list of anatomy areas for display, with at least one of the anatomy areas corresponding to the highlighted area of the patient.

8. The clinical photographic recordkeeping system according to claim 7 wherein the list of anatomy areas further includes at least one of a stock thumbnail and an actual photo thumbnail of the patient for each anatomy area.

9. The clinical photographic recordkeeping system according to claim 1 wherein said clinical photographic recordkeeping application includes a three-dimensional body for display, and selection of an anatomy area on the three-dimensional body corresponds to the highlighted area of the patient.

10. The clinical photographic recordkeeping system according to claim 1 wherein said clinical photographic recordkeeping application includes an opacity feature for reducing an opacity of the at least one existing photo when used as a guide.

11. The clinical photographic recordkeeping system according to claim 1 wherein said clinical photographic recordkeeping application includes an outline feature for outlining the at least one existing photo when used as a guide.

12. The clinical photographic recordkeeping system according to claim 1 wherein said clinical photographic recordkeeping application includes a grid feature for displaying a grid on a camera view corresponding to the new photo of the highlighted area.

13. A portable electronic device comprising:

a housing;

a transceiver carried by said housing and configured to communicate with a remote storage device;

a display carried by said housing;

a camera carried by said housing;

a processor carried by said housing and coupled to said transceiver, said display and said camera, said processor configured to execute a clinical photographic recordkeeping application to perform the following display a patient list from the remote storage device based on a user logging into the clinical photographic recordkeeping application, select a patient from the patient list based on a first user input, and display at least one image showing a highlighted area of the selected patient to be photographed, with the at least one image including a flag indicating that the patient has at least one existing photo on the remote storage device of the highlighted area to be photographed; and said camera configured to take a new photo of the highlighted area of the patient based on a second user input while said processor is further configured to display the at least one existing photo of the highlighted area for the user to use as a guide when taking the new photo of the highlighted area.

14. The portable electronic device according to claim 13 wherein said clinical photographic recordkeeping application includes a list of anatomy areas for display, with at least one of the anatomy areas corresponding to the highlighted area of the patient.

15. The portable electronic device according to claim 13 wherein said clinical photographic recordkeeping application includes a three-dimensional body for display, and selection of an anatomy area on the three-dimensional body corresponds to the highlighted area of the patient.

16. The portable electronic device according to claim 13 wherein said clinical photographic recordkeeping application includes an opacity feature for reducing an opacity of the at least one existing photo when used as a guide.

17. The portable electronic device according to claim 13 wherein said clinical photographic recordkeeping application includes an outline feature for outlining the at least one existing photo when used as a guide.

18. The portable electronic device according to claim 13 wherein said clinical photographic recordkeeping application includes a grid feature for displaying a grid on a camera view corresponding to the new photo of the highlighted area.

19. A method for operating a clinical photographic recordkeeping system comprising a remote storage device, and at least one portable electronic device comprising a housing, a transceiver carried by the housing and configured to communicate with the remote storage device, a display carried by the housing, a camera carried by the housing, and a processor carried by the housing, the method comprising:

storing a patient list and a plurality of patient photos at the remote storage device;

operating the processor to execute a clinical photographic recordkeeping application to perform the following         display the patient list from the remote storage device based on a user logging into the clinical photographic recordkeeping application,         select a patient from the patient list based on a first user input,         display at least one image showing a highlighted area of the selected patient to be photographed, with the at least one image including a flag indicating that the patient has at least one existing photo on the remote storage device of the highlighted area to be photographed; and     operating the camera to take a new photo of the highlighted area of the patient based on a second user input while the processor displays the at least one existing photo of the highlighted area for the user to use as a guide when taking the new photo of the highlighted area.

20. The method according to claim 19 wherein the remote storage device is configured as a cloud-based storage device.

21. The method according to claim 19 wherein the clinical photographic recordkeeping application includes a list of anatomy areas for display, with at least one of the anatomy areas corresponding to the highlighted area of the patient.

22. The method according to claim 19 wherein the clinical photographic recordkeeping application includes a three-dimensional body for display, and selection of an anatomy area on the three-dimensional body corresponds to the highlighted area of the patient.

23. The method according to claim 19 wherein the clinical photographic recordkeeping application includes an opacity feature for reducing an opacity of the at least one existing photo when used as a guide.

24. The method according to claim 19 wherein the clinical photographic recordkeeping application includes an outline feature for outlining the at least one existing photo when used as a guide.

\* \* \* \* \*